United States Patent [19]

Gubler et al.

[11] Patent Number: 4,618,700
[45] Date of Patent: Oct. 21, 1986

[54] PROCESS FOR THE PREPARATION OF A HYDROXYPHENYLCARBOXYLATE

[75] Inventors: Erich Gubler, Birsfelden; Max Siegrist, Lausen, both of Switzerland

[73] Assignee: Ciba-Geigy Corporation, Ardsley, N.Y.

[21] Appl. No.: 680,687

[22] Filed: Dec. 12, 1984

[30] Foreign Application Priority Data

Dec. 22, 1983 [CH] Switzerland .......................... 6858/83

[51] Int. Cl.$^4$ .............................................. C07C 69/88
[52] U.S. Cl. .......................................... 560/67; 560/75
[58] Field of Search ..................... 560/67, 75

[56] References Cited

U.S. PATENT DOCUMENTS 3,644,482  2/1972  Dexter .................................. 560/75

Primary Examiner—Paul J. Killos
Attorney, Agent, or Firm—Harry Falber

[57] ABSTRACT

Pentaerythrityl tetrakis-[3-(3,5-di-tert-butyl-4-hydroxyphenyl)propionate] is prepared by transesterifying a lower alkyl 3-(3,5-di-tert-butyl-4-hydroxyphenyl)propionate with pentaerythritol in the presence of a basic catalyst, without addition of an inert solvent and in a 15 to 50% excess of lower alkyl 3-(3,5-di-tert-butyl-4-hydroxyphenyl)propionate over the stoichiometric amount of 4 moles per 1 mole of pentaerythritol.

An extremely good yield of pure crystalline product is obtained by the process of the invention.

8 Claims, No Drawings

PROCESS FOR THE PREPARATION OF A HYDROXYPHENYLCARBOXYLATE

The present invention relates to a process for the preparation of crystalline pentaerythrityl tetrakis-[3-(3,5-di-tert-butyl-4-hydroxyphenyl)propionate] by transesterifying an excess of lower alkyl 3-(3,5-di-tert-butyl-4-hydroxyphenyl)propionate with pentaerythritol in the absence of an inert solvent.

A process for the preparation of pentaerythrityl tetrakis-[3-(3,5-di-tert-butyl-4-hydroxyphenyl)propionate] by reacting 2,6-di-tert-butylphenol with methacrylate and transesterifying the methyl 3-(3,5-di-tert-butyl-4-hydroxyphenyl)propionate obtained as intermediate with pentaerythritol, in tetraline, as described in U.S. Pat. spec. No. 4,228,297. However, the yield obtained in this process is unsatisfactory. Another process for the preparation of pentaerythrityl tetrakis-[3-(3,5-di-tert-butyl-4-hydroxyphenyl)propionate] is described in U.S. Pat. No. 3,644,482. In this process, the transesterification of methyl 3-(3,5-di-tert-butyl-4-hydroxyphenyl)-propionate with pentaerythritol is carried out with a 9.1% excess of ester but without an inert solvent. The advantage of using a 5 to 10% excess of ester is explained in the general description. The process affords a glass-like substance, and the yield is also unsatisfactory.

Surprisingly, it has now been found that crystalline pentaerythrityl tetrakis-[3-(3,5-di-tert-butyl-4-hydroxyphenyl)propionate] is obtained in excellent yield by carrying out the transesterification with a 15 to 50% excess of lower alkyl 3-(3,5-di-tert-butyl-4-hydroxyphenyl)propionate over the stoichiometric amount of 4 moles per 1 mole of pentaerythritol, without the addition of an inert solvent.

Accordingly, the present invention relates to a process for the preparation of pentaerythrityl tetrakis-[3-(3,5-di-tert-butyl-4-hydroxyphenyl)propionate] by transesterifying a lower alkyl 3-(3,5-di-tert-butyl-4-hydroxyphenyl)propionate with pentaerythritol, in the presence of a catalytic amount of a basic catalyst, which process comprises carrying out the transesterification with a 15 to 50%, preferably 25 to 35% excess of said lower alkyl 3-(3,5-di-tert-butyl-4-hydroxyphenyl)propionate over the stoichiometric amount of 4 moles per 1 mole of pentaerythritol.

Lower alkyl denotes $C_1$–$C_4$alkyl, e.g. methyl, ethyl, propyl, isopropyl and n-butyl, with methyl being preferred.

The catalyst is preferably used for example in amounts from 0.5 to 10 mol %, most preferably from 1.0 to 6 mol %, based on pentaerythritol.

Suitable catalysts are the conventional basic catalysts employed for transesterification reactions, for example alkali metal amides such as lithium amide, alkali metal hydrides such as lithium hydride, alkali metal hydroxides such as potassium hydroxide or sodium hydroxide, alkali metal alcoholates such as sodium methylate or sodium ethylate, as well as the oxides of metals of the fourth main or auxiliary group of the Periodic Table, for example those of the formula I $$(R_1O)_4—M \qquad (I)$$

wherein $R_1$ is $C_1$–$C_{18}$alkyl, phenyl or benzyl, and M is the element Ge, Zr or Sn, or those of the formula II

wherein $R_2$ is $C_4$–$C_{12}$alkyl.

$R_2$ as $C_4$–$C_{12}$alkyl is e.g. n-butyl, n-pentyl, n-hexyl, n-octyl, n-decyl or n-dodecyl. $R_1$ as $C_1$–$C_{18}$alkyl has the same meaning as $R_2$ and is, in addition, e.g. methyl, ethyl, propyl, isopropyl, n-hexadecyl and n-octadecyl. $R_1$ and $R_2$ are preferably n-butyl.

Preferred catalysts are dibutyltin oxide and, in particular, lithium amide.

The transesterification is conveniently carried out in the temperature range from 120° to 220° C., preferably from 140° to 200° C., and under a pressure of 30 to 1 mbar, preferably from 10 to 2 mbar.

The lower alkanol formed during the transesterification is removed by vacuum distillation. Excess lower alkyl 3-(3,5-di-tert-butyl-4-hydroxyphenyl)propionate is distilled off under vacuum at the conclusion of the reaction (it can be re-used for the next batch), and the hot melt of pentaerythrityl tetrakis-[3-(3,5-di-tert-butyl-4-hydroxyphenyl)propionate] is clarified by filtration and then crystallised by conventional methods, preferably from a lower alkanol, preferably methanol, which is slightly acidified with acetic acid.

The starting materials and catalysts are known commercially available substances.

The process of this invention is distinguished by the extremely good yield of pure crystalline product which has exceptionally good flowability. A further advantage of this process is that it is carried out without a solvent.

Pentaerythrityl tetrakis-[3-(3,5-di-tert-butyl-4-hydroxyphenyl)propionate] is a known stabiliser for organic materials which are subject to degradation, for example for synthetic organic polymers, animal and vegetable oils, hydrocarbons, lubricants and the like.

The invention is illustrated by the following non-limitative Examples.

EXAMPLE 1

A 6300 liter vessel is charged with 5010 kg (17.15 kmol=30 mol %, based on pentaerythritol) of methyl 3-(3,5-di-tert-butyl-4-hydroxyphenyl)propionate (abbreviated hereinafter to methyl ester) as a melt of about 80° C., 450 kg (3.3 kmol) of pentaerythritol and 3 kg (0.13 kmol=4 mol %, based on pentaerythritol) of lithium amide. With stirring, the mixture is heated to 150° C. over 100 minutes under a pressure of about 200 mbar. At 120°–125° C. methanol begins to distill into a receiver vessel. As soon as about 380 liters of methanol are distilled off, full vacuum is applied and the batch is heated to about 200° C. Methyl ester begins to boil under reflux at about 175° C. and 80 mbar. A vacuum of 7 to 10 mbar and a temperature of 198° C. is then gradually attained, while methanol is removed through the vacuum pump. The methyl ester reflux is maintained for ½ hour and then excess methyl ester is distilled off into a receiver vessel. At the conclusion of the distillation, i.e. after about 8 hours, the vacuum is 3 to 5 mbar, the temperature is 200° C. and the amount of methyl ester is 1080 kg. The methyl ester which has distilled off is re-used for another batch.

The hot reaction melt is clarified by filtration at 180°–200° C. and then crystallised by charging it into methanol which is slightly acidified with acetic acid. Yield: 3700 kg (95.0% of theory) of crystalline pentaerythrityl tetrakis-[3-(3,5-di-tert-butyl-4-hydroxyphenyl)propionate] with a melting point of 118°–119° C.

EXAMPLES 2 AND 3

The procedure of Example 1 is repeated, with the sole exception that the excess of methyl ester is varied as indicated in Table 1.

TABLE 1

| Example | Excess of methyl ester in mol %, based on pentaerythritol | Yield | m.p. |
| --- | --- | --- | --- |
| 2 | 20 | 88.3 | 114 |
| 3 | 50 | 91.9 | 114 |

EXAMPLES 4 TO 10

The procedure of Example 1 is repeated using other catalysts in different ratios at different temperatures, pressures and excesses of methyl ester, as shown in Table 2.

TABLE 2

| Example | Catalyst | Amount of catalyst in mol. % based on pentaerythritol | Temperature (°C.) | Pressure (mbar) | Amount of methyl ester in mol. % based on pentaerythritol | Yield | m.p. (°C.) |
| --- | --- | --- | --- | --- | --- | --- | --- |
| 4 | lithium hydride | 2.5 | 150 | 3 | 45 | 90.9 | 114 |
| 5 | lithium hydride | 4.25 | 150 | 3 | 45 | 93.7 | 114 |
| 6 | Na—ethylate | 2.5 | 190 | 30 | 45 | 79.7 | 113 |
| 7 | dibutyltinoxide | 0.5 | 190 | 3 | 15 | 91.3 | 115 |
| 8 | dibutyltinoxide | 6.0 | 190 | 3 | 21 | 86.3 | 114 |
| 9 | dibutyltinoxide | 10.0 | 190 | 3 | 21 | 82.4 | 117 |
| 10 | dibutyltinoxide | 1.25 | 190 | 10 | 21 | 96.7 | 114 |

What is claimed is:

1. A process for the preparation of pentaerythrityl tetrakis-[3-(3,5-di-tert-butyl-4-hydroxyphenyl)propionate] by transesterifying a lower alkyl 3-(3,5-di-tert-butyl-4-hydroxyphenyl)propionate with pentaerythritol, in the presence of a catalytic amount of a basic catalyst, which process comprises carrying out the transesterification with a 15 to 50% excess of lower alkyl 3-(3,5-di-tert-butyl-4-hydroxyphenyl)propionate over the stoichiometric amount of 4 moles per 1 mole of pentaerythritol.

2. A process according to claim 1, wherein a 25 to 35% excess of lower alkyl 3-(3,5-di-tert-butyl-4-hydroxyphenyl)propionate over the stoichiometric amount of 4 moles per 1 mole of pentaerythritol is used.

3. A process according to claim 1, wherein lower alkyl is methyl.

4. A process according to claim 1, wherein the catalyst is used in an amount of 0.5 to 10 mol %, based on pentaerythritol.

5. A process according to claim 1, wherein lithium amide or dibutyltin oxide is used as catalyst in an amount of 1.0 to 6 mol.%, based on pentaerythritol.

6. A process according to claim 5, wherein lithium amide is used as catalyst.

7. A process according to claim 1, wherein the transesterification is carried out in the temperature range from 120° to 220° C.

8. A process according to claim 1, wherein the transesterification is carried out under a pressure of 30 mbar to 1 mbar.

* * * * *